United States Patent [19]

Evers et al.

[11] Patent Number: 4,845,286
[45] Date of Patent: Jul. 4, 1989

[54] ACETYLENE TERMINATED AROMATIC AMIDE MONOMERS

[75] Inventors: Robert C. Evers, Dayton; Tonson Abraham, Elyria; Edward J. Soloski, Dayton, all of Ohio

[73] Assignee: The United States of America as represented by the Secretary of the Air Force, Washington, D.C.

[21] Appl. No.: 89,652

[22] Filed: Aug. 24, 1987

[51] Int. Cl.$^4$ ............................................. C07C 103/00
[52] U.S. Cl. ..................................... 564/154; 564/162; 564/174
[58] Field of Search ......................... 564/154, 162, 174

[56] References Cited

PUBLICATIONS

Abraham et al., "Acetylene–Terminated Aromatic Amide Resin Precursors": CA 105 209411r (1986).

Primary Examiner—Glennon H. Hollrah
Assistant Examiner—A. A. Owens
Attorney, Agent, or Firm—Charles E. Bricker; Donald J. Singer

[57] ABSTRACT

Provided is an acetylene-terminated aromatic amide compound of the formula

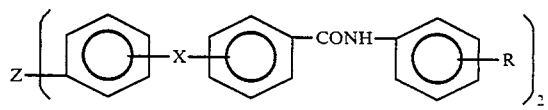

wherein X is —O— or —S—, Z is —O—, —S—, —SO$_2$—, or —CO—, and R is —H or —C≡CH in the ortho, meta or para position, wherein at least one R is —C≡CH.

7 Claims, No Drawings

ACETYLENE TERMINATED AROMATIC AMIDE MONOMERS

RIGHTS OF THE GOVERNMENT

The invention described herein may be manufactured and used by or for the Government of the United States for all governmental purposes without the payment of any royalty.

BACKGROUND OF THE INVENTION

This invention relates to acetylene-termninated aromatic amide monomers.

Acetylene-terminated compounds, with phenylene-R backbones (e.g. phenylene ether, phenylene sulfone, and the like) show promise for use in the preparation of matrix resins and adhesives for composite structures. The compounds can be polymerized thermally without the evolution of volatile by-products, thereby obviating the problem of void formation in composite structures and molded articles. These compounds tend to lack toughness, possibly due to the relatively short phenylene-R backbones between the acetylene cure sites.

It is an object of the present invention to provide novel acetylene-terminated compounds.

It is another object of the present invention to provide a method for producing novel acetylene-terminated comounds.

Other objects and advantages of the present invention will become apparent to those skilled in the art from a reading of the following disclosure.

SUMMARY OF THE INVENTION

In accordance with the present invention there is provided an acetylene-terminated aromatic amide compound of the formula

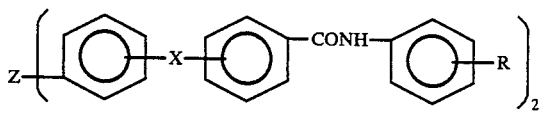

wherein X is —O— or —S—, Z is —O—, —S—, —SO$_2$—, or —CO—, and R is —H or —C≡CH in the ortho, meta or para position, wherein at least one R is —C≡CH.

DESCRIPTION OF THE PREFERRED EMBODIMENTS

The compounds of this invention are prepared by first reacting a bis(fluorophenyl) compound with a hydroxybenzoic acid or a mercaptobenzoic acid as shown by the reaction

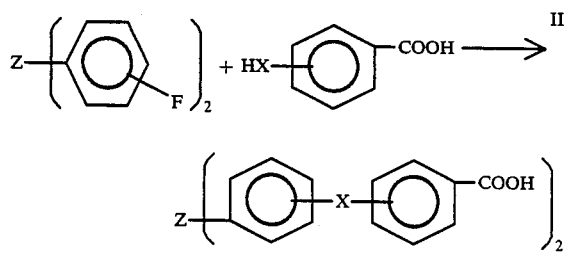

The terms Z and X are described previously. Suitable bis(fluorophenyl) compounds include bis(4-fluorophenyl) sulfone, 4,4'-difluoro-benzophenone, 4,4'-difluorophenyl ether and 4,4'-difluorophenyl sulfide. The reaction may be carried out under anhydrous conditions in a suitable aprotic solvent such as dimethyl formamide or dimethyl sulfoxide at an elevated temperature of about 80°–130° C. for about 2-36 hours to provide the dibenzoic acid II.

The dibenzoic acid II is then converted to its corresponding carbonyl halide as shown by the reaction

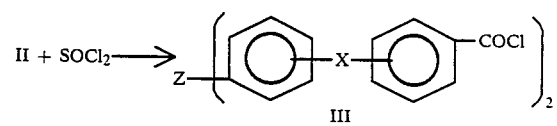

This reaction may be carried out by refluxing the dibenzoic acid II in a thionyl halide, such as thionyl chloride, for about 1 to 8 hours, to provide the corresponding dicarbonyl halide III.

The dicarbonyl halide III is converted to the acetylene-terminated compound I by reacting III with an amino phenyl acetylene as shown by the following

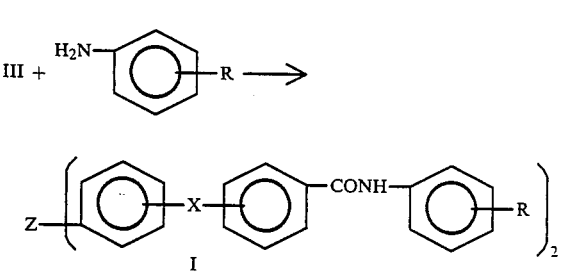

The above reaction may be carried out by combining the reactants at a controlled rate at a reduced temperature, e.g. about 0°–10° C. in a suitable solvent, such as tetrahydrofuran under an inert atmosphere.

The acetylene-terminated compounds I of this invention can be thermally homopolymerized by heating the monomers in an inert or oxidizing atmosphere at a temperature of about 150°–300° C. A heating period of about 1-2 hours is usually sufficient to obtain a complete cure although longer periods, e.g., up to 24 hours, many be used.

While it not intended to be limited to any particular theory, it is believed that in the curing step the terminal ethynyl groups propagate to form polyenes.

The following examples illustrate the invention

EXAMPLE I 3,3'-{Sulfonylbis(p-phenyleneoxy)}dibenzoic acid

A mixture of m-hydroxybenzoic acid; (6.5g, 47.1 mmol), 4,4'-sulfonyldifluorobenzene (5.98g, 23.5 mmol), and 26 g of anhydrous potassium carbonate in 100 ml of anhydrous dimethyl sulfoxide (distilled from CaH$_2$ under vacuum) was stirred by paddle and maintained under nitrogen at 120° C. for 24 hrs.

After cooling, a solution was obtained by pouring the reaction slurry into approximately 300 ml of water. Approximately 100 ml of concentrated hydrochloric acid was then added slowly to the cooled (ice bath) solution. On the addition of the concentrated hydrochloric acid the white precipitate that formed was filtered off after being allowed to stand in the cold bath for ½ hr. The lumpy residue was broken up and washed with copious amounts of water. Recrystallization from dilute acetic acid gave 3,3'-{sulfonylbis(p-phenyleneoxy)}dibenzoic acid as white crystals (Dried overnight at 60° C. at 0.1 mm Hg); 9.65g, 83%; m.p. 175°–200° C.). A sample of the product with m.p. 219°–220° C. could not be purified further by recrystallization from dilute acetic acid. Calculated for $C_{26}H_{18}O_8S$: C,63.66; H,3.69; S,6.63. Found: C,63.58; H,3.67; S,6.48.

EXAMPLE II 3,3'-{Sulfonylbis(p-phenyleneoxy)}dibenzoyl chloride

A suspension of 3,3'{sulfonylbis(p-phenyleneoxy)}dibenzoic acid (16.2, 33.0 mmol) in 130 ml of thionyl chloride was refluxed under nitrogen for 4 hrs. The suspension dissolved as the reaction progressed. Excess thionyl chloride was initially removed by distillation at atmospheric pressure, followed by the application of a vacuum. The glassy residue was difficult to crystallize. However, after standing 48 hrs in a dry box, the residue readily crystallized from a solution of anhydrous tetrahydrofuran (distilled from sodium/benzophenone) and heptane. 3,3'-{Sulfonylbis(p-phenyleneoxy)}dibenzoyl chloride was obtained as white crystals (Dried overnight at 50° C. at 0.1 mm Hg); 15.8 g, 90%; m.p. 113°–116° C. Recrystallization raised the melting point to 116°–116.5° C., which could not be improved further by recrystallization. Calculated for $C_{26}H_{16}Cl_2O_6S$: C,59.21; H,3.05; Cl,13.44; S,6.08. Found: C,59.01; H,2.91; Cl,13.42; S,6.10.

EXAMPLE III 3,3'-{Carbonylbis(p-phenyleneoxy)}dibenzoic acid

Using the procedure of Example I, the crude carbonyldiacid was obtained by heating a mixture of m-hydroxybenzoic acid (12.0 g, 94.2 mmol), 4,4'-carbonyldi(fluorobenzene) (10.27 g, 47.1 mmol), and anhydrous potassium carbonate (52.0 g) in 190 ml of anhydrous dimethylsulfoxide at 120° C. for 48 hrs under nitrogen.

The crude product was boiled in approximately 400 ml of glacial acetic acid, and the boiling solution was filtered to remove suspended solids. The residue obtained weighted 2.4 g (m.p. 263°–65°). On cooling, the filtrate yielded 13.3 g (m.p. 257°–61°) of white crystals. This lower melting material was treated as before with approximately 200 ml of glacial acetic acid to give a residue (4.7 g, m.p. 261°–263°) and white crystals (7.0 g, m.p. 260°–62°). All samples were dried at 80° C. (0.1 mm Hg). The combined purer fractions weighed 14.1 g(65%). Calculated for $C_{27}H_{18}O_7$; C,71.36; H,3.99. Found: C,70.93; H, 4.03.

EXAMPLE IV 3,3'-{Carbonylbis(p-phenyleneoxy)}dibenzoic chloride

Using the procedure of Example II, the title diacid chloride was obtained in 47% yield (m.p. 137°–140° C.) Calculated for $C_{27}H_{16}O_5Cl_2$: C,66.00; H, 3.28; Cl, 14.43. Found C, 66.25; H, 3.34; Cl, 14.25.

EXAMPLE V

N,N'-2-Ethynylphenyl-3,3'-{sulfonyl bis(p-phenyleneoxy)}dibenzamide

A solution of 3,3'-{sulfonylbis(p-phenyleneoxy)}dibenzoyl chloride (6.0 g, 11.4 mmol) in 50 ml of anhydrous tetrahydrofuran (distilled under nitrogen from sodium/benzophenone) was added dropwise under nitrogen to a cooled (ice bath) solution of 2-aminophenylacetylene (3.0g, 25.6 mmol) in 12 ml of anhydrous triethylamine (distilled under nitrogen from calcium hydride) and 20 ml of anhydrous tetrahydrofuran. A white precipitate of triethylamine hydrochloride appeared as the addition progressed. After all the acid chloride was added, the reaction mixture was stirred for three hours at room temperature. Water was then added and the aqueous phase extracted with methylene chloride. The methylene chloride solution was washed with water, thoroughly with cold (ice bath) 2N hydrochloric acid, water, and aqueous sodium bicarbonate, in that order. After drying the organic layer (MgSO4), a", colorless oil resulted on removing the solvent by rotary evaporator. A glassy white foam appeared when residual solvents were removed by vacuum pump at room temperature. The foam was broken up and maintained under vacuum for 24 hours at room temperature. The title compound thus obtained weighed 7.5g (95%). The product, however, was contaminated with residual tetrahydrofuran which could not be removed by vacuum at room temperature. Warming the compound during vacuum drying was not attempted in order to avoid possible polymerization via the terminal acetylene groups. Calculated for $C_{42}H_{28}N_2O_6S$: C,73.24; H,4.09; N,4.06; S,4.65. Found: C,72.49; H,4.06; N,4.24; S,4.53.

EXAMPLE VI

A series of monomers having the formula

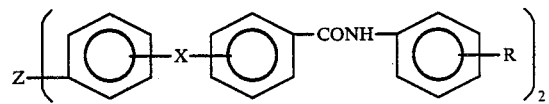

was prepared following the procedure of Example V. The identification of Z and R are given in Table I below.

TABLE I

| Monomer | Z | R |
|---|---|---|
| Ia | —SO2— | o-C≡CH (Example V) |
| Ib | —SO2— | m-C≡CH |
| Ic | —SO2— | p-C≡CH |
| IIa | —CO— | o-C≡CH |
| IIb | —CO— | m-C≡CH |
| IIc | —CO— | P-C≡CH |

The acetylene-terminated aromatic amides Ia-IIc were obtained as glassy white solids. Infrared spectra indicated absorptions corresponding to the N-H (3300–3415 cm$^{-1}$), C≡C—H(3300–3310 cm$^{-1}$). C≡C(2100–2115 cm$^{-1}$), and C═O (1645–1680 cm$^{-1}$) stretching vibrations. The N-H stretching vibration moved to lower frequency as the acetylene substitution changed from ortho, to meta, and then to para, presumably attributable to differences in intra- or inter-molecular hydrogen bonding. Proton nuclear magnetic resonance spectra (CDCl$_3$, TMS) were also consistent with the proposed structures. Observed were singlets at 3.05–3.62 ppm (2 protons) attributable to acetylenic protons, complex multiplets at 6.70–8.62 ppm (24 protons) attributable to aromatic protons, and singlets at 8.49–8.82 ppm (2 protons) indicative of the amide protons. As was noted with the infrared spectral data, differences in spectra were observed between the ortho-, meta-, and para-substituted acetylene compounds. Mass spectra of monomers Ia-c and IIa-c, while exhibiting parent ion peaks only with ortho-substituted monomers Ia and IIa, were consistent with the proposed structures in respect to fragmentation patterns. High performance liquid chromatography indicated purity of greater than 96% for all the monomers with compounds Ia-c which contain the sulfone moiety (Z=SO$_2$) being somewhat purer than their carbonyl-containing (Z=CO) analogs IIa-c.

The thermal characteristics of the monomers Ia-c and IIa-c were investigated by means of differential scanning calorimetry under a nitrogen atmosphere and thermogravimetric analysis (TGA) in air. Results of these tests are summarized in Table II below. All temperatures are expressed in °C.

TABLE II

| | Thermal Analytical Data | | | |
|---|---|---|---|---|
| Monomer Tg (initial) | T (cure onset) | T (cure max.) | Tg$^{(a)}$ (final) | T$^{(b)}$ (onset dec.) |
| Ia 59 | 100 | 251 | 185 | 435 |
| Ib — | 209 | 234 | 247 | 444 |
| Ic 40 | 195 | 227 | — | 450 |
| IIa 29 | 209 | 259 | 194 | 400 |
| IIb 49 | 225 | 243 | — | 483 |
| IIc 182 | 182 | 201 | — | 436 |

$^{(a)}$After cycling to 450° C.
$^{(b)}$Extrapolated from TGA in air

With the exception of Ib and IIc, the initial Tg's of the monomers were well below the onset of cure and indicated an adequate processing "window." Onset of cure occurred in the 160°–225° C. range. With the exception of ortho-substituted monomers Ia and IIa, the monomers upon heating to 450° C. either exhibited a significantly higher Tg (Ib) or did not exhibit a Tg up to the onset of decomposition (Ic, IIb, and IIc).

The thermooxidative stabilities of the cured resins were evaluated by TGA. Onset of weight loss in an air atmosphere ocurred in the 400°–485° C. range with essentially no weight residues being present at 700° C. The extrapolated values for onset of weight loss are summarized in Table II.

It will be evident to those skilled in the art that modifications of the present invention can be made in view of the foregoing disclosure without departing from the spirit and scope of the invention.

We claim:
1. An acetylene-terminated aromatic amide compound of the formula:

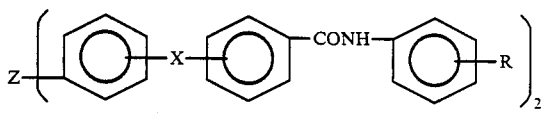

wherein X is —O— or —S—, Z is —O—, —S—, —CO— or —SO$_2$—, and R is H or —C≡CH in the ortho, meta or para position, and wherein at least one R is —C≡CH.

2. The compound of claim 1 wherein X is —O—, Z is —SO$_2$— and R is in the ortho position.

3. The compound if claim 1 wherein X is —O—, Z is —SO$_2$—and R is in the meta position.

4. The compound if claim 1 wherein X is —O—, Z is —SO$_2$— and R is in the para position.

5. The compound of claim 1 wherein X is —O—, Z is —CO— and R is in the ortho position.

6. The compound of claim 1 wherein X is —O—, Z is —CO— and R is in the meta position.

7. The compound of claim 1 wherein X is —O—, Z is —CO— and R is in the para position.

* * * * *